US008187574B2

(12) United States Patent
Mekata et al.

(10) Patent No.: US 8,187,574 B2
(45) Date of Patent: May 29, 2012

(54) INTERMITTENT INJECTION AEROSOL PRODUCT FOR SKIN

(75) Inventors: Satoshi Mekata, Ibaraki (JP); Hiroshi Fujio, Saitama (JP)

(73) Assignee: Dazio Corporation, Osaka (JP)

( * ) Notice: Subject to any disclaimer, the term of this patent is extended or adjusted under 35 U.S.C. 154(b) by 2273 days.

(21) Appl. No.: 11/004,363

(22) Filed: Dec. 3, 2004

(65) Prior Publication Data

US 2005/0100512 A1 May 12, 2005

Related U.S. Application Data

(62) Division of application No. 10/018,515, filed as application No. PCT/JP01/03181 on Apr. 13, 2001, now abandoned.

(30) Foreign Application Priority Data

Apr. 17, 2000 (JP) ................................. 2000-115030

(51) Int. Cl.

| | |
|---|---|
| ***A61K 9/12*** | (2006.01) |
| *A61K 8/00* | (2006.01) |
| *B65B 1/04* | (2006.01) |
| *B67C 3/00* | (2006.01) |
| *B65D 25/40* | (2006.01) |
| *B65D 35/38* | (2006.01) |
| *B65D 83/14* | (2006.01) |
| *G01F 11/04* | (2006.01) |
| *G04C 23/42* | (2006.01) |
| *B67D 7/14* | (2010.01) |
| *A61M 35/00* | (2006.01) |
| *A61M 37/00* | (2006.01) |

(52) U.S. Cl. ............ 424/45; 424/47; 141/347; 141/371; 222/3; 222/56; 222/59; 222/64; 222/145.1; 222/249; 222/328; 222/335; 222/395; 222/399; 222/491; 222/494; 222/635; 604/24; 604/289; 604/290; 604/310; 604/311

(58) Field of Classification Search .................... 424/45, 424/47; 222/3, 56, 59, 64, 145.1, 328, 335, 222/395, 399, 635

See application file for complete search history.

(56) References Cited

U.S. PATENT DOCUMENTS 3,696,809 A * 10/1972 Moret ........................... 601/162
3,787,566 A * 1/1974 Gauvreau et al. ............... 424/45
3,788,521 A * 1/1974 Laauwe .......................... 222/94

(Continued)

FOREIGN PATENT DOCUMENTS

EP 0 532 349 A2 3/1993

(Continued)

OTHER PUBLICATIONS

English abstract for JP 07-096226.

(Continued)

*Primary Examiner* — Johann Richter
*Assistant Examiner* — Jane C Oswecki
(74) *Attorney, Agent, or Firm* — Ware, Fressola, Van Der Sluys & Adolphson, LLP

(57) ABSTRACT

The present invention is directed to an intermittent aerosol dispensing device, for application of a product to skin of a human being, where the aerosol dispensing device includes an intermittent injection mechanism located downstream of an aerosol valve of an aerosol dispenser and responsive to a pushbutton of the aerosol dispensing device, and the aerosol dispensing device further includes a pressure chamber. A ratio of an injection time to a stop time is set, in said intermittent injection mechanism, to 0.1 to 5.0, so that when said aerosol valve is opened a cycle of injection and stop is performed 1 to 25 times per second in order to obtain a cooling and/or massage effect on the skin.

18 Claims, 3 Drawing Sheets

U.S. PATENT DOCUMENTS

| | | | | | |
|---|---|---|---|---|---|
| 3,863,628 | A * | 2/1975 | Vit | | 433/88 |
| 4,147,284 | A | 4/1979 | Mizzi | | 222/401 |
| 4,175,678 | A | 11/1979 | Fukuda et al. | | 222/54 |
| 4,262,823 | A | 4/1981 | Monden et al. | | 222/321 |
| 4,942,874 | A | 7/1990 | Terada et al. | | 128/203.16 |
| 5,025,962 | A * | 6/1991 | Renfro | | 222/649 |
| 5,170,782 | A | 12/1992 | Kocinski et al. | | 128/200 |
| 5,328,062 | A | 7/1994 | Tubaki et al. | | 222/385 |
| 5,713,349 | A | 2/1998 | Keaney | | 128/204.23 |
| 5,881,925 | A | 3/1999 | Ando et al. | | 222/190 |
| 6,533,141 | B1 * | 3/2003 | Petterson et al. | | 222/1 |

FOREIGN PATENT DOCUMENTS

| | | | |
|---|---|---|---|
| GB | 1573969 | | 8/1980 |
| JP | 63-038468 | A | 2/1988 |
| JP | 02-272084 | | 11/1990 |
| JP | 05213734 | A * | 8/1993 |
| JP | 07-096226 | | 4/1995 |
| JP | 07-187 262 | A | 7/1995 |
| JP | 10235237 | * | 9/1998 |
| JP | 10-278982 | | 10/1998 |
| JP | 11-033444 | | 2/1999 |
| JP | 11-342202 | A | 12/1999 |

OTHER PUBLICATIONS

English abstract for JP 02-272084.
English abstract for JP 11-033444.
Derwent English abstract of JP 07-187 262-A.

* cited by examiner

INTERMITTENT INJECTION AEROSOL PRODUCT FOR SKIN

CROSS-REFERENCE TO RELATED APPLICATIONS

This application is a divisional of U.S. application Ser. No. 10/018,515 filed Dec. 13, 2001, now abandoned which was the U.S. National Stage of International Application No. PCT/JP01/03181 filed Apr 13, 2001 designating the United States and claiming priority to Japanese Application No. 2000-115030 filed Apr. 17, 2000.

TECHNICAL FIELD

The present invention relates to an intermittent injection aerosol product for a skin. More particularly, the present invention relates to an intermittent injection aerosol product for a skin in which an injection time and a stop time are repeated at a specific ratio when an injection button is operated, thereby intermittently injecting a content to a skin including a head skin accurately.

BACKGROUND ART

Conventionally, an injection device includes an aerosol product and a pump product. In the aerosol product, a concentrate and a propellant are filled in a pressure container and continuously carries out injection when a valve is released. The manner of injection of the aerosol product is generally continuous injection, while quantitative injection or intermittent injection is carried out depending on the use and purpose. The aerosol product for the continuous injection is suitably used for injecting a large amount of aerosol in a space or onto a wall surface. In the case in which the aerosol is continuously injected onto a skin, a large amount of liquid drips on the injection surface if a concentrate is blended in a large amount, and cooling properties are so great as to feel a pain if the propellant (liquefied gas) is blended in a large amount. The aerosol product to be quantitatively injected is suitably used for a product having a determined effective component amount which can be utilized at each time for medical and pharmaceutical products or the like, and has no problem about the liquid dripping and the cooling properties. However, in the case in which the effective component amount to be required is large or a massage effect is to be obtained through the energy of the injection, an injection button needs to be pressed many times.

In the aerosol product for the intermittent injection, injection and stop are repeated. In the case in which the aerosol product is used for a human body, stimulation is repeated many times through the energy of the injection and the massage effect can be obtained in addition to the effect of medicament.

Depending on an injection time and a stop time, however, a feeling of stimulation is too great or too small, which is not preferable. In particular, preferable injection and stop times are varied depending on an aerosol composition.

On the other hand, the pump product can be injected in a predetermined amount by operating a finger push button for each injection. In the same manner as in the aerosol product for quantitative injection, however, it is necessary to operate a pump many times in order to obtain the massage effect through the energy of the injection. Consequently, a great deal of time and labor is required. Moreover, the pump requires a time for accumulating a pressure to some degree in order to carry out the injection. Therefore, it is hard to carry out the intermittent injection at a small interval.

In consideration of the above-mentioned circumstances, it is an object of the present invention to provide an intermittent injection aerosol product for a skin in which an injection time and a stop time are repeated at a specific ratio when an injection button is operated, thereby intermittently injecting a content onto a skin including a head skin accurately and obtaining an excellent massage effect.

DISCLOSURE OF INVENTION

An intermittent injection aerosol product for a skin of the present invention is characterized in that a ratio of an injection time to a stop time is set to 0.1 to 5.0 when an injection button is operated.

Moreover, an intermittent injection aerosol product for a skin of the present invention is characterized in that the product contains 20 to 70% by weight of a liquefied gas in an aerosol composition, and that a ratio of an injection time to a stop time is 0.1 to 5.0 when an injection button is operated.

Furthermore, an intermittent injection aerosol product for a skin of the present invention is characterized in that the product contains 0.1 to 5% by weight of a compressed gas in an aerosol composition, and that a ratio of an injection time to a stop time is 0.1 to 2.0 when an injection button is operated.

BEST MODE FOR CARRYING OUT THE INVENTION

Figure 1:
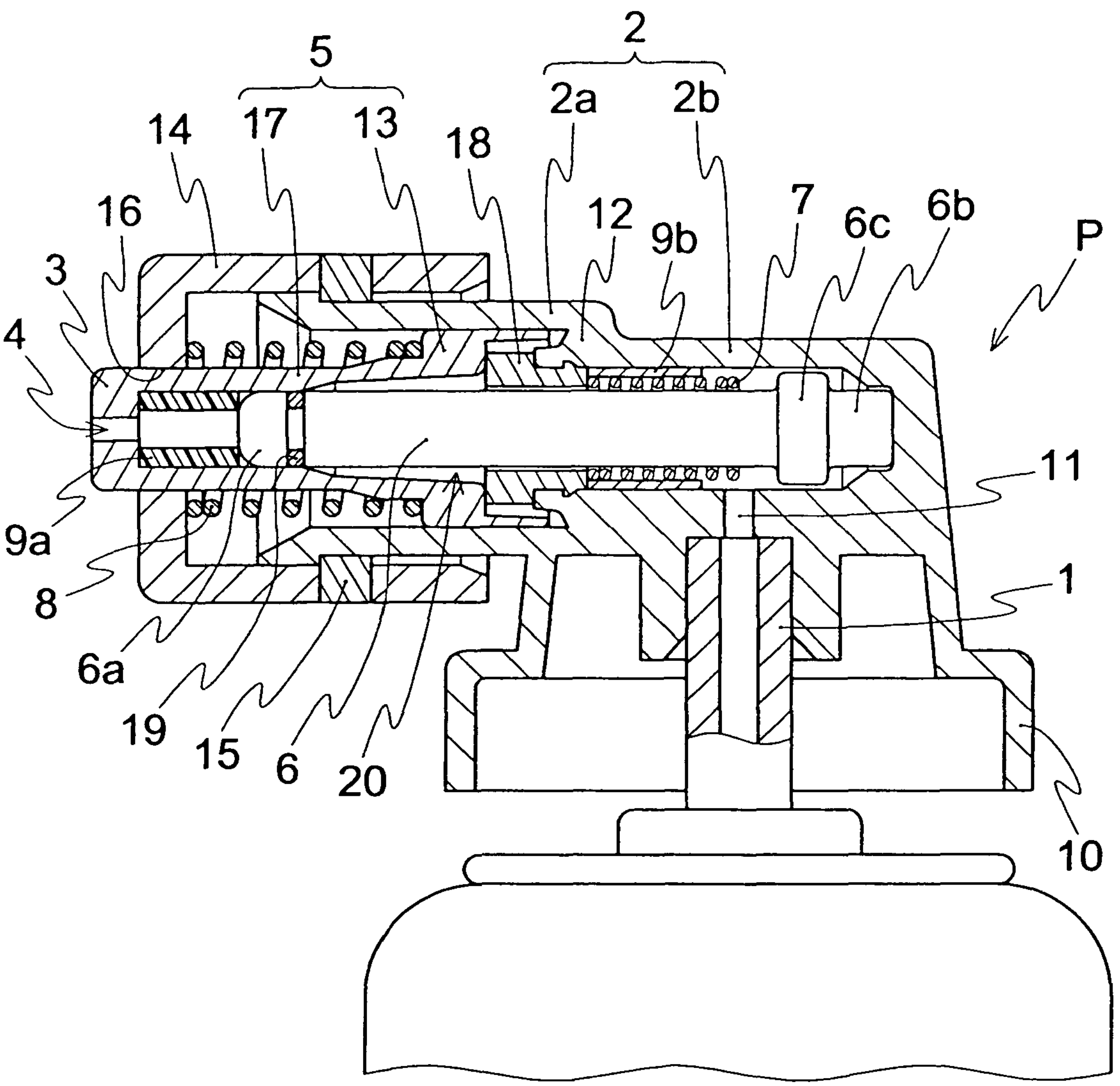
FIG. 1 is a partial sectional view showing an intermittent injection aerosol product for a skin according to an embodiment of the present invention.

In an intermittent injection aerosol product for a skin according to the present invention, a ratio of an injection time to a stop time is 0.1 to 5.0, and preferably, 0.5 to 4.0. When the ratio of the injection time to the stop time is 0.1 to 5.0, stimulation caused by the energy of injection and stop are properly repeated when an aerosol composition is injected onto a skin. Consequently, an excellent massage effect can be obtained. On the other hand, when the ratio of the injection time to the stop time is less than 0.1, the stop time is long or the injection time is short. Therefore, there is a problem that a long time is required for injecting a predetermined amount of medicament or a massage effect is reduced. Moreover, when the ratio of the injection time to the stop time is more than 5.0, the stop time is short or the injection time is long. Therefore, a state close to continuous injection is brought and supercooling cannot be prevented.

In the case of an aerosol product containing 20 to 70% by weight of a liquefied gas in an aerosol composition, furthermore, it is preferable that the ratio of the injection time to the stop time is 0.1 to 5.0, and furthermore, 0.1 to 4.5. Within such a range, supercooling can be prevented from being caused by vaporization heat of the liquefied gas and a feeling of refreshment can be obtained by proper cooling. When the ratio of the injection time to the stop time is less than 0.1, the stop time is long or the injection time is short. Therefore, the vaporization heat quantity of the liquefied gas is small and a proper feeling of cooling cannot be obtained. On the other hand, when the ratio is more than 5.0, the injection time is long or the stop time is short. Therefore, the vaporization heat quantity of the liquefied gas is too large so that the supercooling is caused to feel a pain.

Moreover, when the amount of the liquefied gas contained in the aerosol composition is less than 20% by weight, mist-like injection is hard to perform and liquid dripping is increased over an injection surface. Moreover, if the aerosol composition is homogeneous, the pressure of the product is reduced. Therefore, pressure accumulation in a pressure chamber which will be described below is delayed and the ratio of the injection time to the stop time easily becomes less than 0.1. Moreover, even if the ratio of the injection time to the stop time is 0.1 to 5.0, both the injection time and the stop time are increased, and injection in a short cycle is not carried out, for example, one cycle or more is not set for one second. In some cases, therefore, the massage effect is reduced.

On the other hand, when the amount of the liquefied gas is more than 70% by weight in the aerosol composition, a feeling of cooling is too increased so that a feeling of use is deteriorated. Moreover, since the pressure of the product is raised, the stop time is shortened and the ratio of the injection time to the stop time easily exceeds 5.0. Further, even if the ratio of the injection time to the stop time is 0.1 to 5.0, both the injection time and the stop time are shortened and a cycle of injection and stop exceeds 25 times for one second so that the state close to the continuous injection is brought.

In the case of an aerosol product containing 0.1 to 5% by weight of a compressed gas in the aerosol composition, it is preferable that the ratio of the injection time to the stop time is 0.1 to 2.0, and furthermore, 0.2 to 1.5. Within such a range, liquid dripping over an injection surface can be prevented. Thus, the feeling of use can be more excellent than that in a conventional aerosol product using the compressed gas, and furthermore, a massage effect can be obtained. When the ratio of the injection time to the stop time is less than 0.1, the massage effect is reduced. When the ratio exceeds 2.0, the liquid dripping is caused easily.

When the amount of the compressed gas contained in the aerosol product is less than 0.1% by weight, the pressure of the product is dropped. Therefore, the pressure accumulation in the pressure chamber is delayed and the ratio of the injection time to the stop time easily becomes less than 0.1. In the case of the compressed gas, moreover, the pressure of the product is reduced with the injection. In some cases, consequently, the injection cannot be carried out when the amount of the aerosol composition in the aerosol container is decreased.

Moreover, even if the ratio of the injection time to the stop time is 0.1 to 2.0, both the injection time and the stop time are increased and the injection cannot be carried out in a short cycle, for example, a cycle of three times or more for one second is not set. In some cases, therefore, the massage effect is reduced.

On the other hand, when the amount of the compressed gas contained in the aerosol composition exceeds 5% by weight, the pressure of the product is raised. Therefore, the pressure accumulation in the pressure chamber is carried out quickly and the ratio of the injection time to the stop time easily exceeds 2.0.

Moreover, even if the ratio of the injection time to the stop time is 0.1 to 2.0, both the injection time and the stop time are shortened. For example, a cycle is set to 20 times or more for one second and the state close to the continuous injection is brought.

The aerosol composition to be used in the present invention includes a concentrate containing an effective component and a propellant. In the concentrate, the effective component is dissolved or dispersed in a solvent and other components are added thereto corresponding to the configuration of a product or uses. The aerosol product is used for a product for a human body (for a skin and a head skin). More specifically, the aerosol product is used for a skin care, a cleansing agent, a moisturizing agent, a deodorizer, an aromatic, an anodyne and antiphlogistic, an astringent, an antipruritic, a tonic, a repellent and the like.

0.1 to 20% by weight of the effective component is contained in the aerosol composition. If the amount is less than 0.1% by weight, a desirable effect cannot be obtained and the amount of injection is increased to obtain a necessary amount. If the amount is more than 20% by weight, further blending does not influence the effect.

In the case in which the propellant is a liquefied gas, it is contained in an amount of 20 to 70% by weight. If the amount is less than 20% by weight, it is hard to carry out the injection with a mist. If the amount is more than 70% by weight, a feeling of cooling is too increased and a feeling of use becomes poor. Moreover, since injection particles are too small, they easily scatter over the skin or the head skin and a user might suck the particles, which is not preferable.

On the other hand, in the case in which the propellant is a compressed gas, it is contained in an amount of 0.1 to 5% by weight. If the amount is less than 0.1% by weight, the pressure of a product is small and the injection cannot be completed. If the amount is more than 5% by weight, the pressure of the product is too increased, which might be dangerous.

If the propellant is the liquefied gas, the pressure of the product is 0.2 to 0.7 MPa (25° C.). If the pressure is less than 0.2 MPa, the stop time is long and the ratio of the injection time to the stop time cannot be set to be a predetermined ratio If the pressure is more than 0.7 MPa, the continuous injection is easily carried out. Moreover, there is a possibility that the pressure might exceed 0.8 MPa at 35° C., which deviates from the condition of exempt from the application of the high pressure gas safety law.

On the other hand, in the case in which the propellant is the compressed gas, the pressure is 0.2 to 1.0 MPa (25° C.). If the pressure is less than 0.2 MPa, the stop time is long and the ratio of the injection time to the stop time cannot be set to be a predetermined ratio. Moreover, when the contents are decreased, the injection cannot be completed. If the pressure is more than 1.0 MPa, the continuous injection is easily carried out.

The effective component includes a moisturizing agent, an ultraviolet absorber, a skin softener, amino acid, vitamins, hormones, an antioxidant, various extracted solutions, a fungicide and antiseptic, a deodorant, an antiperspirant, an anodyne and antiphlogistic, a refrigerant, an astringent, an anti-inflammatory, a local anesthetic, an antihistaminics, a whitening agent, chemicals for a tonic, a repellent, a perfume and the like.

The moisturizing agent includes polyethylene glycol, propylene glycol, glycerin and the like.

The ultraviolet absorbent includes benzoic acid such as paraaminobenzoate or monoglyserine ester paraaminobenzoate, anthranilic acid such as methyl anthranilate, and the like.

The skin softener includes urea and the like.

The amino acid includes neutral amino acid such as glycine, acidic amino acid such as aspartic acid, basic amino acid such as arginine and the like.

The vitamins include vitamin A oil, retinol, retinol palmitate, acetic acid dl-α-tocopherol and the like.

The hormones include elastoradiol, ethynyl elastoradiol and the like.

The antioxidant includes ascorbic acid, α-tocopherol, dibutylhydroxytoluene and the like.

The various extracted solutions include houttuynia extract, phellodendron bark extract, sweet clover extract, placental extract and the like.

The fungicide and antiseptic includes ester paraoxybenzoate, benzoic acid, sodium benzoate and the like.

The deodorant includes lauryl methacrylate, geranil crotolate, acetophenone myristate, a green tea extracted solution and the like.

The antiperspirant includes chlorhydroxy aluminum, zinc oxide, aluminum chloride and the like.

The anodyne and antiphlogistic includes methyl salicylate, camphor, diphenhydramine and the like.

The refrigerant includes 1-menthol, camphor and the like.

The astringent includes zinc oxide, allantoin hydroxyaluminum, tannic acid and the like.

The anti-inflammatory includes allantoin, glythyl retinate, azulene and the like.

The local anesthetic includes dibucaine hydrochloride, tetracaine hydrochloride, lidocaine hydrochloride and the like.

The antihistaminics includes diphenhydramine hydrochloricde, chlorfemiramine maleate and the like.

The whitening agent includes arbutin, kojic acid and the like.

The chemicals for tonic include a blood circulation accelerator such as swertia herb extract, a local stimulant such as capsicum tincture, a hairy root activator such as pantothenic acid and the like.

The repellent includes N, N-diethyl-m-toluamide (deet), diethylamide caprylate and the like.

The propellant includes liquefied petroleum gas (butane, propane and their mixture), a liquefied gas such as dimethyl ether, tetrafluoroethane or difluoroethane, and a compressed gas such as a nitrogen gas, carbon dioxide, compressed air, or a dinitrogen monoxide gas.

Other components include a surfactant such as sorbitan fatty acid ester, glycerin fatty acid ester or decaglycerin fatty acid ester; ester oil such as isopropyl myristate, cetyl octanate or octyldodecyl myristate; silicone such as dimethyl polysiloxane, methylphenyl polysiloxane or methylhydrogen polysiloxane; oils and fats such as avocado oil, camellia oil or turtle oil; higher fatty acid such as lauric acid, myristic acid or palmitic acid; wax such as beeswax, lanolin or lanolin acetate; higher alcohol such as lauryl alcohol, cetyl alcohol or stearyl alcohol; a high molecular compound such as agar, casein or dextrin; powder such as talc, silica, zinc oxide or titanium oxide; a pH regulator such as lactic acid, citric acid or glycolic acid, and the like.

The solvent includes water such as purified water or ion-exchange water, lower alcohol such as ethanol, propanol or isopropanol, polyhydric alcohol such as glycerin, ethylene glycol, propylene glycol or 1,3-butyleneglycol, hydrocarbon such as isoparaffin, liquid paraffin, normal pentane, isopentane or normal hexane, and the like.

In the present invention, an aerosol device shown in FIG. 1 can be used to set the ratio of the injection time to the stop time to be 0.1 to 5.0, for example.

An intermittent injection aerosol product for a skin according to the present invention will be described below with reference to the accompanying drawings.

Figure 2A:
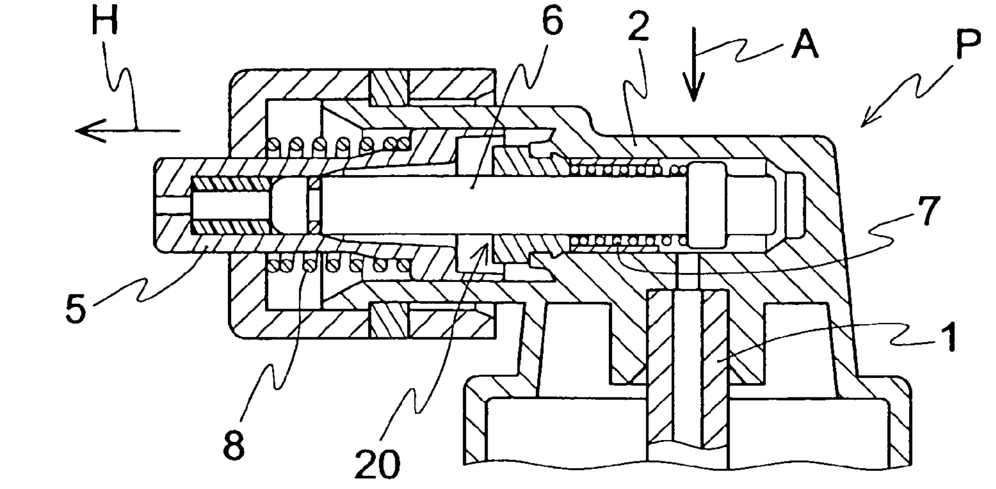
FIG. 2 is a view illustrating the operation of an intermittent injection mechanism in an aerosol device shown in FIG. 1.
Figure 2B:
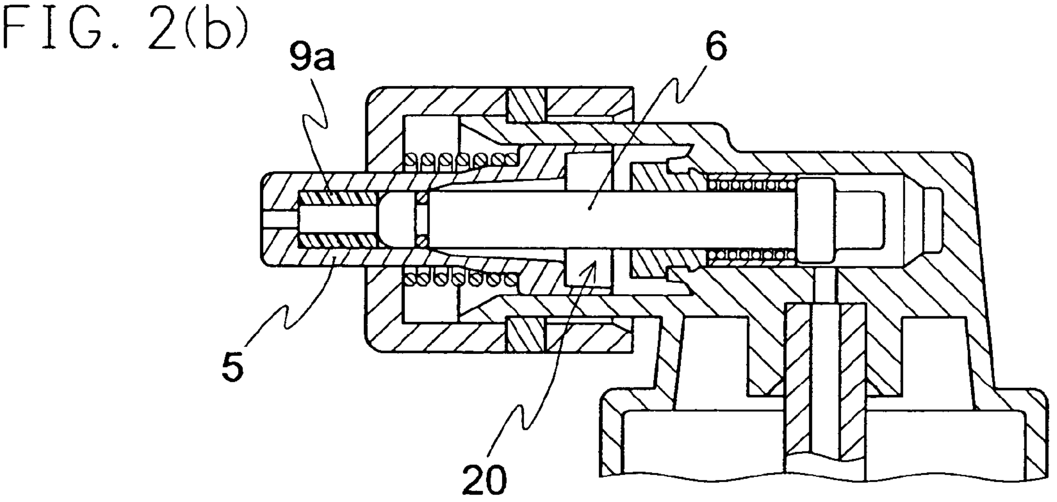

FIG. 1 is a partial sectional view showing an intermittent injection aerosol product for a skin according to an embodiment of the present invention, and FIG. 2 is a view illustrating the operation of an intermittent injection mechanism in the aerosol product shown in FIG. 1.

As shown in FIG. 1, the aerosol product according to the embodiment of the present invention includes an intermittent injection mechanism in an injection button (push button) P attached to a valve stem 1. The intermittent injection mechanism comprises a cylinder 2 fitted in the valve stem 1, a piston 5 having an injection port 4 formed on a tip wall 3, a needle valve 6 for opening and closing the injection port 4, a second coil spring 7 for energization in such a direction as to open the needle valve 6, and a first coil spring 8 for energizing the piston 5 in such a direction as to close the needle valve 6, and a regulation member 9*a* is provided between the tip wall 3 of the piston 5 and a tip portion 6*a* of the needle valve 6 and a regulation member 9*b* which is shorter than the second coil spring is provided on the outer periphery of the second coil spring.

In the present embodiment, such regulation members 9*a* and 9*b* are provided. Consequently, when the injection button P is operated, the injection time and the stop time are repeated at a specific ratio so that intermittent injection can be carried out accurately.

More specifically, when the regulation member 9*a* is provided, the positions of the inside of the piston and an O ring are fixed. Moreover, the regulation member 9*b* is provided so that the distance of movement of the needle valve is fixed. Consequently, a timing of valve opening and closing is stabilized. Accordingly, injection and stop can be carried out clearly and the intermittent injection can be performed accurately.

Although the materials for the regulation members 9*a* and 9*b* are not particularly limited, it is possible to use a resin such as nylon, polyacetal or polyethylene terephthalate.

The injection button P is provided with a skirt portion 10 to surround and protect the valve stem 1, and an inlet port 11 communicating with the cylinder 2 is formed in the-fitting portion of the valve stem 1. The piston 5, the needle valve 6, the second coil spring 7, the first coil spring 8 and the like are accommodated in the cylinder 2.

The cylinder 2 is divided into a large diameter portion 2*a* on the tip side (the left side in the drawing) and a small diameter portion 2*b* on the rear end side (the right side in the drawing) through a step portion 12 formed on the inside thereof, and the piston 5 and the cylindrical needle valve 6 having the tip portion 6*a* fitted therein through the opening of a rear end funnel-shaped portion 13 of the piston 5 are slidably inserted in the large diameter portion 2*a* concentrically with the cylinder 2, respectively. Moreover, a cap 14 having a hole is fastened to the outer peripheral portion of the tip of the cylinder 2 with a pin 15, and the tip portion of the piston 5 is protruded from a tip hole 16.

The piston 5 includes a tip cylindrical portion 17 and the funnel-shaped portion 13 having an inside diameter increased continuously from a middle portion, and the outer peripheral surface of the funnel-shaped portion 13 is provided airtightly in slidable contact with the inner peripheral surface of the large diameter portion 2*a* and the funnel-shaped portion 13 abuts on a stopper 18 fastened to the step portion 12.

The first coil spring 8 for energizing the piston 5 in a valve closing direction, that is, a rightward direction in the drawing is wound around the outer periphery of the piston 5 in a compression state between the cap 14 and the outer peripheral step portion of the funnel-shaped portion 13 of the piston 5 in the large diameter portion 2*a* of the cylinder 2.

The needle valve 6 penetrates through the central opening of the stopper 18 with a small clearance provided therearound, and an O ring 19 for slidably coming in contact with the inner peripheral surface of the piston 5 airtightly is fitted and attached into the outer peripheral groove of the tip portion 6*a*. A step portion 6*c* is formed on a rear end 6*b*. By sliding the outer peripheral surface of the step portion 6*c* over the inner peripheral surface of the small diameter portion 2*b*, a stable sliding characteristic can be obtained. The clearance can be appropriately adjusted.

The second coil spring 7 is wound around the outer periphery of the needle valve 6 in a free length state between the stopper 18 and the step portion 6*c* of the needle valve 6. The second coil spring 7 serves to be flexed when both the piston 5 and the needle valve 6 are moved in a leftward direction in the drawing, thereby applying energizing force to only the needle valve 6 in a valve opening direction (the rightward direction in the drawing). The second coil spring 7 is incorporated in the free length state such that the needle valve 6 can be moved together with the piston 5 while displaying a sealing function through the O ring 19 by the pressure of a content. It is possible to change and set an initial flex in relation to the selection of the spring constant of the second coil spring 7.

In the aerosol product according to the present embodiment, consequently, the piston 5 is positioned on the rightmost end in the drawing of a stroke through the first coil spring 8 and the inside of the cylinder 2 is set in an airtight state with respect to the outside through the O ring 19 provided between the inner peripheral surface of the piston 5 and the tip portion 6*a* of the needle valve 6, and the abutment of the tip face of the needle valve 6 and the regulation member 9. In this case, the inside of the cylinder 2 will be particularly referred to as a pressure chamber 20. The rear end funnel-shaped portion 13 of the piston 5 abuts on the stopper 18. The needle valve 6 is set in such a state that the rear end 6*b* abuts on the side wall surface of the cylinder 2. The second coil spring 7 is set in a free length state, so that force thereof is not particularly applied to the needle valve 6.

Next, the operation of the intermittent injection mechanism in the aerosol product according to the present embodiment will be described with reference to FIGS. 1 and 2.

First of all, FIG. 1 shows the state (valve closing state) in which the intermittent injection mechanism does not carry out an injecting operation.

Subsequently, when the injection button P is pushed down (a direction of an arrow A), the valve stem 1 is pressed downward so that an aerosol valve (not shown) is opened, thereby the content flows into the pressure chamber 20 in the cylinder 2. As shown in FIG. 2(*a*), consequently, the piston 5 and the needle valve 6 are moved together in a direction of an arrow H while flexing the first and second coil springs 8 and 7 by a difference between an internal pressure applied by the content and an external air pressure. As shown in FIG. 2(*b*), finally, the needle valve 6 is stopped to be moved by the abutment of the step portion 6*c* on the regulation member 9*b*. However, the first coil spring 8 is still set in a flexing state. Therefore, the piston 5 is further moved and the sealing state of the piston 5 and the needle valve 6 is released at this time so that a clearance for causing the outside to communicate with the pressure chamber 20 is generated between the piston 5 and the needle valve 6.

By the regulation member 9*b*, the stop position of the needle valve is always constant, and furthermore, the position of the tip (O ring) of the needle valve in a cylindrical portion of the tip of the piston is also constant. Therefore, such a timing that the sealing is released is always constant.

Figure 2C:
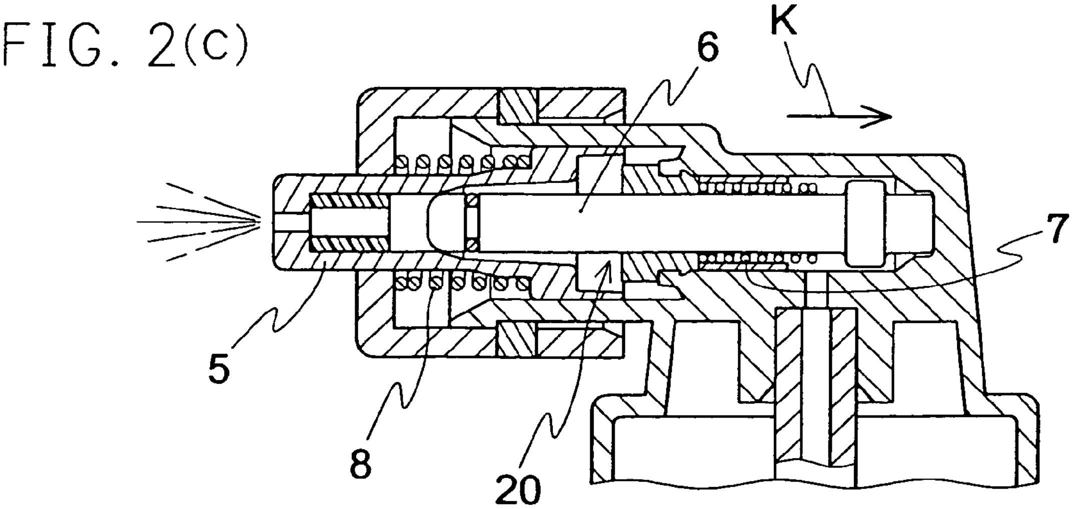

As shown in FIG. 2(C), subsequently, when the content is injected toward the outside through the clearance, the pressure of the pressure chamber 20 is started to be dropped such that the piston 5 is returned in the valve closing direction through the first coil spring 8 without fully injecting the content. However, the difference between a pressure on the tip side of the needle valve 6 and a pressure on the rear end side thereof is reduced simultaneously with the injection of the content. Therefore, the needle valve 6 is repelled in a direction of an arrow K through the second coil spring 7 and is thereby pushed back to a position shown in the drawing. As a result, an injection passageway for the content can be sufficiently maintained until the piston 5 is returned to the valve closing position (the position shown in FIG. 1).

Accordingly, the injection is continuously carried out for a constant time and the internal pressure of the pressure chamber 20 is sufficiently dropped when the piston 5 is returned to the valve closing position. As a result, a constant time is required for recovering the internal pressure of the pressure chamber 20 to such a pressure as to generate the injection again, and the valve closing state is maintained. After the internal pressure is recovered, the content is injected again. Consequently, the intermittent injection can be obtained. Moreover, the valve can also be opened or closed by sending a signal to control a driving mechanism such as a motor by using an external personal computer or the like, for example, in addition to the above-mentioned aerosol device.

While examples of the present embodiment will be described below, the present invention is not limited to only the following examples.

EXAMPLES 1 to 5

An aerosol composition consisting of 50% by weight of a concentrate containing 50% by weight of purified water and 50% by weight of ethanol, and 50% by weight of dimethyether (DME) to be a liquefied gas was filled in a pressure container formed of aluminum so that an aerosol product was obtained. Subsequently, the aerosol product was preserved under the condition of each temperature and an injection time and a stop time were measured by the following method.

Figure 3:
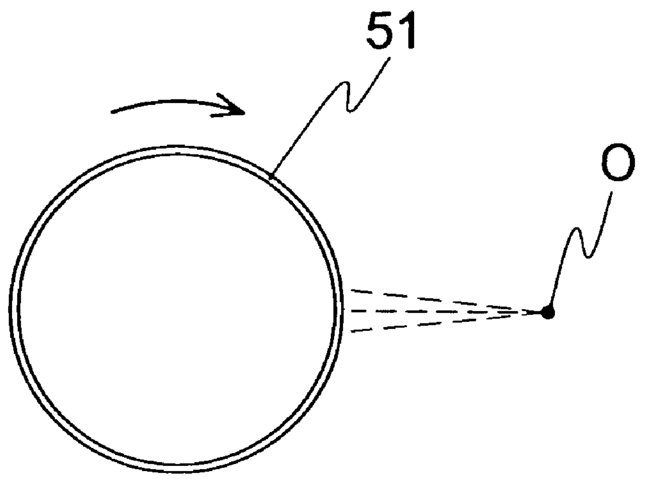
FIG. 3 is a view illustrating a method of measuring an injection time and a stop time.

An aerosol valve having a stem hole of ϕ0.3 mm and a housing lower hole of ϕ0.3 mm was used and the injection button shown in FIG. 1 was used. A spring including a first spring having a load of 480 g and a second spring having a load of 180 g was used for the injection button, and a piston hole diameter is 1.0 mm. First of all, as shown in FIG. 3, the following is carried out.

1. A photosensitive paper 51 is applied onto the outside of a cylinder having a diameter of 300 mm.
2. The number of rotations of the cylinder is set to one rotation/second.

Accordingly, the cylinder has a circumference of 2πr=942 mm and movement is carried out by 942 mm per second.

Figure 4:
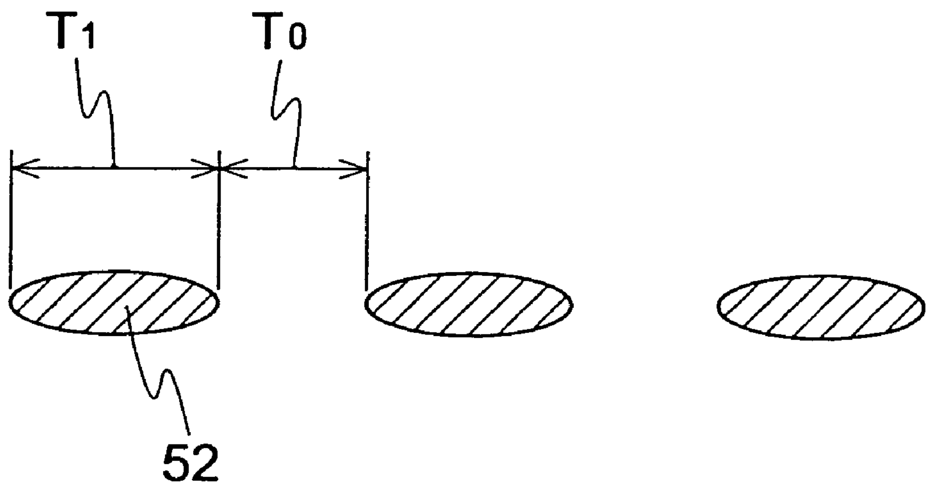
FIG. 4 is a view illustrating an injection track and the measurement of the injection time and the stop time.

3. The cylinder is rotated to inject the aerosol product to be a test body in a position of a 0 point (a distance of 10 cm from the 10 photosensitive paper). As shown in FIG. 4, in an injection track 52, an injection time $T_1$ (=y/942, y is a measured distance) and a stop time $T_0$ were alternately measured. The distance is an average for five continuous times and is set to a maximum value when the measurement is carried out five times or less per second.

The result is shown in Table 1.

TABLE 1

| Concentrate/ DME | | Ex. 1 | Ex. 2 | Ex. 3 | Ex. 4 | Ex. 5 |
|---|---|---|---|---|---|---|
| | | Preservation temperature (°C.) | | | | |
| (weight ratio) | | 5 | 15 | 25 | 30 | 35 |
| 50/50 | Product pressure (MPa) | 0.21 | 0.27 | 0.40 | 0.43 | 0.49 |

TABLE 1-continued

| Concentrate/ DME (weight ratio) | | Ex. 1 | Ex. 2 | Ex. 3 | Ex. 4 | Ex. 5 |
|---|---|---|---|---|---|---|
| | | Preservation temperature (°C.) | | | | |
| | | 5 | 15 | 25 | 30 | 35 |
| | Injection time (second) | 0.032 | 0.043 | 0.03 | 0.028 | 0.034 |
| | Stop time (second) | 0.224 | 0.088 | 0.023 | 0.013 | 0.008 |
| | Injection/stop | 0.14 | 0.49 | 1.30 | 2.15 | 4.25 |
| | Cycle (times/second) | 3.9 | 7.6 | 18.9 | 24.4 | 23.8 |

EXAMPLES 6 to 10

The same concentrate as that in Example 1 was filled in a pressure container formed of aluminum and a nitrogen gas to be a compressed gas was filled to a predetermined product pressure shown in Table 2 to obtain an aerosol product. In the same manner, an injection time and a stop time were measured. The result is shown in Table 2.

TABLE 2

| | Ex. 6 | Ex. 7 | Ex. 8 | Ex. 9 | Ex. 10 |
|---|---|---|---|---|---|
| Product pressure (MPa) | 0.20 | 0.30 | 0.50 | 0.70 | 0.90 |
| Compressed gas weight (%) | 0.23 | 0.32 | 0.51 | 0.68 | 0.86 |
| Injection time (second) | 0.032 | 0.038 | 0.041 | 0.046 | 0.051 |
| Stop time (second) | 0.143 | 0.133 | 0.069 | 0.052 | 0.041 |
| Injection/stop | 0.22 | 0.29 | 0.59 | 0.88 | 1.24 |
| Cycle (times/second) | 5.7 | 5.8 | 9.1 | 10.2 | 10.9 |

EXAMPLES 11 to 13

An aerosol composition (Example 11) containing 60% by weight of the same concentrate as that in Example 1 and 40% by weight of dimethylether, an aerosol composition (Example 12) containing 70% by weight of the same concentrate and 30% by weight of dimethylether, and an aerosol composition (Example 13) containing 40% by weight of the same concentrate and 60% by weight of dimethylether were filled in a pressure container formed of aluminum. Thus, an aerosol product was obtained. The aerosol product thus obtained was maintained at 25° C., the same injection button as that in Example 1 was attached thereto, and an injection time and a stop time were measured in the same manner. The result is shown in Table 3.

EXAMPLES 14 and 15

An aerosol composition (Example 14) containing 50% by weight of ethanol to be a concentrate and 50% by weight of liquefied petroleum gas having a vapor pressure of 0.35 (MPa) at 20° C., and an aerosol composition (Example 15) containing 50% by weight of ethanol and 50% by weight of liquefied petroleum gas having a vapor pressure of 0.40 (MPa) at 20° C. were filled in a pressure container formed of aluminum so that an aerosol product was obtained. The aerosol product thus obtained was maintained at 25° C. and the same injection button as that in Example 1 was attached. In the same manner, an injection time and a stop time were measured. The result is shown in the Table 3.

TABLE 3

| | Ex. 11 | Ex. 12 | Ex. 13 | Ex. 14 | Ex. 15 |
|---|---|---|---|---|---|
| Product pressure (MPa) | 0.33 | 0.27 | 0.44 | 0.39 | 0.42 |
| Injection time (second) | 0.030 | 0.031 | 0.031 | 0.033 | 0.030 |
| Stop time (second) | 0.051 | 0.083 | 0.011 | 0.021 | 0.016 |
| Injection/stop | 0.59 | 0.37 | 2.82 | 1.57 | 1.88 |
| Cycle (times/second) | 12.3 | 8.8 | 23.8 | 18.5 | 21.7 |

COMPARATIVE EXAMPLE 1

An aerosol composition consisting of 20% by weight of a concentrate containing 50% by weight of purified water and 50% by weight of ethanol and 80% by weight of dimethylether to be a liquefied gas was filled in a pressure container so that an aerosol product was obtained. In the same manner as in Example 1, an injection time and a stop time were measured. The result is shown in Table 4.

COMPARATIVE EXAMPLE 2

An aerosol composition consisting of 85% by weight of a concentrate containing 50% by weight of purified water and 50% by weight of ethanol and 15% by weight of dimethylether to be a liquefied gas was filled in a pressure container so that an aerosol product was obtained. In the same manner as in Example 1, an injection time and a stop time were measured. The result is shown in Table 4.

COMPARATIVE EXAMPLE 3

The same concentrate as that in Example 1 was filled in a pressure container and 1.05% by weight of a nitrogen gas was then filled as a compression gas so that an aerosol product was obtained. In the same manner as in Example 1, an injection time and a stop time were measured. The result is shown in the Table 4.

COMPARATIVE EXAMPLE 4

The same concentrate as that in Example 1 was filled in a pressure container and 0.18% by weight of a nitrogen gas was then filled as a compression gas so that an aerosol product was obtained. In the same manner as in Example 1, an injection time and a stop time were measured. The result is shown in the Table 4.

TABLE 4

| | Com. Ex. 1 | Com. Ex. 2 | Com. Ex. 3 | Com. Ex. 4 |
|---|---|---|---|---|
| Product pressure (MPa) | 0.45 | 0.14 | 1.10 | 0.15 |
| Injection time (second) | 0.038 | 0.028 | 0.092 | 0.022 |
| Stop time (second) | 0.005 | 0.336 | 0.018 | 0.245 |
| Injection/stop | 7.60 | 0.08 | 5.11 | 0.09 |
| Cycle (times/second) | 23.3 | 2.7 | 9.1 | 3.7 |

Next, a feeling of use was evaluated. A test sample in each of Examples 1 to 15 and Comparative Examples 1 to 4 was injected into an arm and the following items were evaluated. The result is shown in Tables 5 to 8.

TABLE 5

| | Ex. 1 | Ex. 2 | Ex. 3 | Ex. 4 | Ex. 5 |
|---|---|---|---|---|---|
| Feeling of stimulation | A | A | A | A | A |
| Feeling of cooling | A | A | A | A | A |
| Feeling of use | A | A | A | A | A |

TABLE 6

| | Ex. 6 | Ex. 7 | Ex. 8 | Ex. 9 | Ex. 10 |
|---|---|---|---|---|---|
| Feeling of stimulation | A | A | A | A | A |
| Feeling of cooling | — | — | — | — | — |
| Feeling of use | A | A | A | A | A |

TABLE 7

| | Ex. 11 | Ex. 12 | Ex. 13 | Ex. 14 | Ex. 15 |
|---|---|---|---|---|---|
| Feeling of stimulation | A | A | A | A | A |
| Feeling of cooling | A | A | A | A | A |
| Feeling of use | A | A | A | A | A |

TABLE 8

| | Com. Ex. 1 | Com. Ex. 2 | Com. Ex. 3 | Com. Ex. 4 |
|---|---|---|---|---|
| Feeling of stimulation | C | B | C | B |
| Feeling of cooling | C | B | — | — |
| Feeling of use | D | C | C | B |

Feeling of stimulation

A: A good feeling of massage was obtained.

B: The energy of injection was too small and was not satisfied.

C: The energy of injection was so great as to feel a pain.

Feeling of cooling (only the example using a liquefied gas was evaluated)

A: A good feeling of cooling was obtained.

B: A feeling of cooing was not satisfied.

C: A feeling of cooling was so great as to feel a pain.

Feeling of use

A: Liquid dripping was not caused and troubles were not occurred during use.

B: A long time was required for injection in a proper amount.

C: Liquid dripping was considerably caused and convenience for use could not be obtained.

D: Scattering was considerably caused over an injection surface.

Next, the following concentrate was filled in a pressure container and a propellant was then filled. Thus, the aerosol product according to the present invention was obtained. In the same manner as in the above-mentioned examples, the characteristics of the product and the feeling of use were evaluated. The result is shown in Tables 9 and 10.

EXAMPLE 16

| Tonic | |
|---|---|
| <Concentrate> | |
| Extract of Japanese green gentian | 0.5 |
| Capsicum tincture | 0.2 |
| Placental extract | 0.5 |
| Benzalkonium chloride | 0.1 |
| Glycol propylene | 2.0 |
| Ester parahydroxybenzoate | 0.1 |
| Perfume | 0.1 |
| Etanol | 66.5 |
| Purified water | 30.0 |
| Total | 100.0 (% by weight) |
| <Aerosol prescription> | |
| The above-mentioned concentrate | 50.0 |
| Dimetylether | 50.0 |
| Total | 100.0 (% by weight) |

EXAMPLE 17

| Cleansing agent for head skin | |
|---|---|
| <Concentrate> | |
| Light isoparaffine | 50.0 |
| Sorbitan sesquiolate | 1.0 |
| POE(2) oleylether | 1.0 |
| Perfume | 0.1 |
| Ethanol | 30.0 |
| Purified water | 17.9 |
| Total | 100.0 (% by weight) |
| <Aerosol prescription> | |
| The above-mentioned concentrate | 40.0 |
| Dimetylether | 60.0 |
| Total | 100.0 (% by weight) |

EXAMPLE 18

| Anodyne and antiphlogistic | |
|---|---|
| <Concentrate> | |
| Methyl salicylate | 3.0 |
| d1-camphor | 5.0 |
| 1-menthol | 5.0 |
| Perfume | 0.1 |
| Ethanol | 86.9 |
| Total | 100.0 (% by weight) |

-continued

| Anodyne and antiphlogistic | |
|---|---|
| <Aerosol prescription> | |
| The above-mentioned concentrate | 50.0 |
| Liquefied petroleum gas (0.35 MPa at 20° C.) | 50.0 |
| Total | 100.0 (% by weight) |

EXAMPLE 19

| Massage agent for foot sole | |
|---|---|
| <Concentrate> | |
| Glyceryl glytylretinate | 0.1 |
| Lauryl methacrylate | 0.2 |
| Benzalkonium chloride | 0.1 |
| Green tea extract | 0.5 |
| Perfume | 0.1 |
| Ethanol | 99.0 |
| Total | 100.0 (% by weight) |
| <Aerosol prescription> | |
| The above-mentioned concentrate | 60.0 |
| Liquefied petroleum gas (0.35 MPa at 20° C.) | 40.0 |
| Total | 100.0 (% by weight) |

EXAMPLE 20

| Tonic | |
|---|---|
| <Concentrate> | |
| d1-α-tocopheryl acetate | 0.5 |
| Swertia herb extract | 0.5 |
| Pantothenic acid | 0.5 |
| Propylene glycol | 2.0 |
| Perfume | 0.1 |
| Etanol | 56.4 |
| Purified water | 40.0 |
| Total | 100.0 (% by weight) |
| <Aerosol prescription> | |
| The above-mentioned concentrate | 97.5 |
| Carbon dioxide | 2.5 |
| Total | 100.0 (% by weight) |

EXAMPLE 21

| Lotion | |
|---|---|
| <Concentrate> | |
| 1,3-butylene glycol | 5.0 |
| Glycerin | 5.0 |
| Oleyl alcohol | 0.1 |
| POE(20)sorbitan monolaurate | 1.0 |
| Phenoxy ethanol | 0.1 |
| Etanol | 10.0 |
| Purified water | 78.8 |
| Total | 100.0 (% by weight) |
| <Aerosol prescription> | |
| The above-mentioned concentrate | 99.5 |
| Nitrogen gas | 0.5 |
| Total | 100.0 (% by weight) |

TABLE 9

| | Ex. 16 | Ex. 17 | Ex. 18 | Ex. 19 | Ex. 20 | Ex. 21 |
|---|---|---|---|---|---|---|
| Product pressure (MPa) | 0.33 | 0.38 | 0.39 | 0.36 | 0.64 | 0.71 |
| Injection time (second) | 0.032 | 0.029 | 0.031 | 0.030 | 0.043 | 0.045 |
| Stop time (second) | 0.053 | 0.023 | 0.022 | 0.046 | 0.063 | 0.051 |
| Injection/stop | 0.60 | 1.26 | 1.41 | 0.65 | 0.68 | 0.82 |
| Cycle (times/second) | 11.8 | 19.2 | 18.9 | 13.2 | 9.4 | 10.4 |

TABLE 10

| | Ex. 16 | Ex. 17 | Ex. 18 | Ex. 19 | Ex. 20 | Ex. 21 |
|---|---|---|---|---|---|---|
| Feeling of stimulation | A | A | A | A | A | A |
| Feeling of cooling | A | A | A | A | — | — |
| Feeling of use | A | A | A | A | A | A |

INDUSTRIAL APPLICABILITY

According to the present invention, it is possible to intermittently inject a content into a skin including a head skin accurately.

The invention claimed is:

1. An intermittent aerosol dispensing device, for application of a product to skin of a human being, comprising an intermittent injection mechanism located downstream of an aerosol valve (11) of an aerosol dispenser, said intermittent mechanism being responsive to a pushbutton (P) of the aerosol dispensing device, wherein said intermittent aerosol dispensing device comprises a pressure chamber;

said pressure chamber is configured to be airtight relative to an environment positioned outside of said pressure chamber when the aerosol valve is in a closed state, and said pressure chamber is configured to receive a flow of content into said pressure chamber when the aerosol valve is opened;

whereby said pressure chamber communicates with air of said environment due to a difference between a pressure of said flow of content into said pressure chamber and an air pressure of said environment, causing said content to be dispensed;

after dispensing of said content, pressure in said pressure chamber drops, causing dispensing to stop; and after said stoppage of dispensing, pressure in said pressure chamber recovers, causing dispensing of content to resume; and wherein the product contains 0.1% to 5% by weight of a compressed gas in an aerosol composition; and a ratio of an injection time to a stop time is set, in said intermittent mechanism, to 0.1 to 5.0, when said aerosol valve is opened, in order to obtain a cooling and/or massage effect on the skin, and a cycle of injection and stop is performed 1 to 25 times per second.

2. An intermittent aerosol dispensing device, for application of a product to skin of a human being, comprising an intermittent injection mechanism (5, 6, 7, 8) located downstream of an aerosol valve (11) of an aerosol dispenser, said intermittent mechanism being responsive to a pushbutton (P) of the aerosol dispensing device, wherein said intermittent aerosol dispensing device comprises a pressure chamber;

said pressure chamber is allowed to be in an airtight to atmosphere when the aerosol valve is in a closed state, content flowing into said pressure chamber when the aerosol valve is opened;

whereby said pressure chamber communicates with outside air due to a difference between a pressure of said content flown into said pressure chamber and air pressure of atmosphere, causing said content to be dispensed;

after dispensing of said content, pressure in said pressure chamber drops, causing dispensing to stop; and after said stoppage of dispensing, pressure in said pressure chamber recovers, causing dispensing of content to resume; and wherein the product contains 20 to 70% by weight of a liquefied gas in an aerosol composition, and a ratio of an injection time to a stop time is set, in said intermittent mechanism, to 0.1 to 5.0, when said aerosol valve is opened, in order to obtain a sufficient yet not excessive cooling and/or massage effect on the skin.

3. An intermittent aerosol dispensing device, for application of a product to skin of a human being, comprising an intermittent injection mechanism (5, 6, 7, 8) located downstream of an aerosol valve (11) of an aerosol dispenser, said intermittent mechanism being responsive to a pushbutton (P) of the aerosol dispensing device, wherein said intermittent aerosol dispensing device comprises a pressure chamber;

said pressure chamber is allowed to be in an airtight to atmosphere when the aerosol valve is in a closed state, content flowing into said pressure chamber when the aerosol valve is opened;

whereby said pressure chamber communicates with outside air due to a difference between a pressure of said content flown into said pressure chamber and air pressure of atmosphere, causing said content to be dispensed;

after dispensing of said content, pressure in said pressure chamber drops, causing dispensing to stop; and after said stoppage of dispensing, pressure in said pressure chamber recovers, causing dispensing of content to resume; and wherein the product contains 0.1% to 5% by weight of a compressed gas in an aerosol composition, and a ratio of an injection time to a stop time is set, in said intermittent mechanism, to 0.1 to 2.0, when said aerosol valve is opened, in order to obtain a sufficient yet not excessive massage effect on the skin.

4. The dispensing device of claim 1, wherein said product comprises a propellant and a skin care effective component.

5. The dispensing device of claim 1, wherein said product comprises a propellant and a cleansing agent.

6. The dispensing device of claim 1, wherein said product comprises a propellant and an anodyne.

7. The dispensing device of claim 1, wherein said product comprises a propellant and an antiphlogistic.

8. The dispensing device of claim 1, wherein said product comprises a propellant and a pharmaceutical.

9. The intermittent aerosol dispensing device of claim 1, wherein a cycle of injection and stop is performed 1 to 25 times per second.

10. The intermittent aerosol dispensing device of claim 2, wherein a cycle of injection and stop is performed 1 to 25 times per second.

11. The intermittent aerosol dispensing device of claim 3, wherein a cycle of injection and stop is performed 1 to 25 times per second.

12. The dispensing device of claim 1, wherein said product comprises a tonic.

13. The dispensing device of claim 1, wherein said product comprises a massage agent.

14. An intermittent aerosol dispensing device, for application of a product to skin of a human being, comprising an intermittent injection mechanism located downstream of an aerosol valve (11) of an aerosol dispenser, said intermittent mechanism being responsive to a pushbutton (P) of the aerosol dispensing device, wherein said intermittent aerosol dispensing device comprises a pressure chamber;

said pressure chamber is configured to be airtight relative to an environment positioned outside of said pressure chamber when the aerosol valve is in a closed state, and said pressure chamber is configured to receive a flow of content into said pressure chamber when the aerosol valve is opened;

whereby said pressure chamber communicates with air of said environment due to a difference between a pressure of said flow of content into said pressure chamber and an air pressure of said environment, causing said content to be dispensed;

after dispensing of said content, pressure in said pressure chamber drops, causing dispensing to stop; and after said stoppage of dispensing, pressure in said pressure chamber recovers, causing dispensing of content to resume; and wherein the product contains 20% to 50% by weight of a liquefied gas in an aerosol composition; and a ratio of an injection time to a stop time is set, in said intermittent mechanism, to 0.1 to 5.0, when said aerosol valve is opened, in order to obtain a cooling and/or a massage effect on the skin, and a cycle of injection and stop is performed 1 to 25 times per second.

15. The dispensing device of claim 14, wherein said product comprises a tonic.

16. The dispensing device of claim 14, wherein said product comprises a massage agent.

17. The dispensing device of claim 1, wherein said intermittent aerosol dispensing device comprises at least one regulation member.

18. The dispensing device of claim 14, wherein said intermittent aerosol dispensing device comprising at least one regulation member.

* * * * *